(12) United States Patent
Wang et al.

(10) Patent No.: US 9,632,083 B1
(45) Date of Patent: Apr. 25, 2017

(54) RAPID DIAGNOSTIC TEST DEVICE BY DRIVEN FLOW TECHNOLOGY

(71) Applicant: DNT Scientific Research, LLC, San Diego, CA (US)

(72) Inventors: Naishu Wang, Poway, CA (US); Michael Chang Chien, Cerritos, CA (US)

(73) Assignee: DNT Scientific Research, LLC, San Diego, CA (US)

( * ) Notice: Subject to any disclaimer, the term of this patent is extended or adjusted under 35 U.S.C. 154(b) by 0 days.

(21) Appl. No.: 15/130,642

(22) Filed: Apr. 15, 2016

(51) Int. Cl.
*B01L 3/00* (2006.01)
*G01N 33/50* (2006.01)
*G01N 21/01* (2006.01)
*G01N 21/75* (2006.01)
*G01N 33/543* (2006.01)
*G01N 33/558* (2006.01)
*G01N 21/78* (2006.01)
(Continued)

(52) U.S. Cl.
CPC ...... *G01N 33/558* (2013.01); *B01L 3/502715* (2013.01); *B01L 3/502761* (2013.01); *G01N 21/78* (2013.01); *G01N 33/54366* (2013.01); *B01L 2200/02* (2013.01); *B01L 2300/042* (2013.01); *B01L 2300/069* (2013.01); *B01L 2300/0627* (2013.01); *B01L 2300/0825* (2013.01); *B01L 2300/0858* (2013.01); *B01L 2400/0475* (2013.01); *B01L 2400/0487* (2013.01); *G01N 2021/757* (2013.01); *G01N 2021/7759* (2013.01); *G01N 2021/7763* (2013.01); *G01N 2035/00108* (2013.01); *G01N 2035/00128* (2013.01)

(58) Field of Classification Search
CPC ................ G01N 33/558; G01N 21/78; G01N 33/54366; G01N 2035/00108; G01N 2035/00128; B01L 3/502715; B01L 3/502761; B01L 2400/0475; B01L 2400/0487
See application file for complete search history.

(56) References Cited

U.S. PATENT DOCUMENTS 4,299,916 A  11/1981  Litman et al.
4,366,241 A  12/1982  Tom et al.
(Continued)

OTHER PUBLICATIONS

Office Action dated Oct. 7, 2016 from related U.S. Appl. No. 15/196,459, 20 pages.

*Primary Examiner* — Jennifer Wecker
(74) *Attorney, Agent, or Firm* — Innovation Capital Law Group, LLP; Vic Lin

(57) ABSTRACT

A rapid diagnostic test device uses driven flow technology to significantly expedite the testing time of a sample. The rapid diagnostic test device can be used to analyze liquids, such as some body fluids, by using labeled molecular affinity binding, such as immunochromatography. The test device can detect an analyte, such as an antibody or antigen, which may indicate a particular condition, the presence of a particular drug, or the like. The device includes a top and bottom that combine to form a fluid channel through which a fluid is forced from a fluid collector. A press pad in the device may press against a press pad on a test strip to accelerate chemical mixtures to flow from the conjugate color pad of the test strip toward fixed sites along the strip from which readings are taken.

19 Claims, 17 Drawing Sheets

(51) Int. Cl.
   *G01N 21/77*      (2006.01)
   *G01N 35/00*      (2006.01)

(56)         References Cited

U.S. PATENT DOCUMENTS

| | | |
|---|---|---|
| 5,656,503 A | 8/1997 | May et al. |
| 6,140,136 A * | 10/2000 | Lee .................. G01N 33/54366 422/423 |
| 6,403,383 B1 | 6/2002 | Casterlin et al. |
| 6,875,185 B2 | 4/2005 | Wong et al. |
| 7,431,882 B2 | 10/2008 | Parker |
| 7,741,103 B2 | 6/2010 | Guirguis |
| D626,249 S | 10/2010 | Wang et al. |
| 7,879,623 B2 | 2/2011 | Guirguis |
| 7,981,382 B2 | 7/2011 | Wong et al. |
| 8,021,625 B2 | 9/2011 | Wang et al. |
| 8,206,661 B2 | 6/2012 | Vallejo et al. |
| 8,889,424 B2 | 11/2014 | Ehrenkranz et al. |
| 8,916,390 B2 | 12/2014 | Ozcan et al. |
| 9,414,813 B2 | 8/2016 | Engel et al. |
| 2005/0163660 A1 | 7/2005 | Wang |
| 2006/0292700 A1 | 12/2006 | Wang et al. |
| 2007/0065339 A1 | 3/2007 | Huff |
| 2007/0259442 A1 | 11/2007 | Gould et al. |
| 2009/0208371 A1* | 8/2009 | Hannant ............ A61B 10/0045 422/400 |
| 2013/0022517 A1 | 1/2013 | Engel et al. |
| 2015/0173742 A1 | 6/2015 | Palese et al. |
| 2015/0203904 A1* | 7/2015 | Hopper ................. B01L 3/5023 435/6.12 |
| 2015/0211987 A1 | 7/2015 | Burg et al. |
| 2016/0025752 A1* | 1/2016 | Santiago ................ G08C 17/02 436/501 |

* cited by examiner

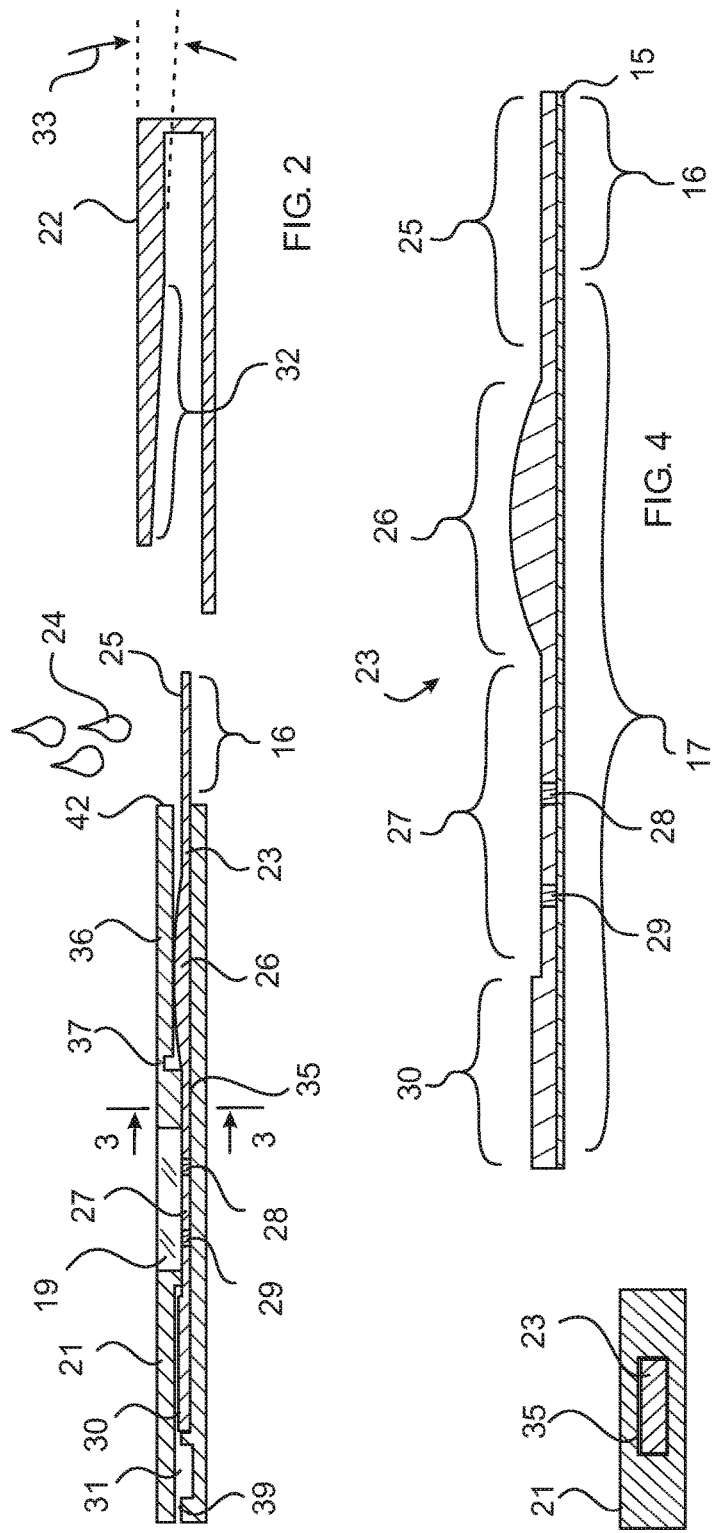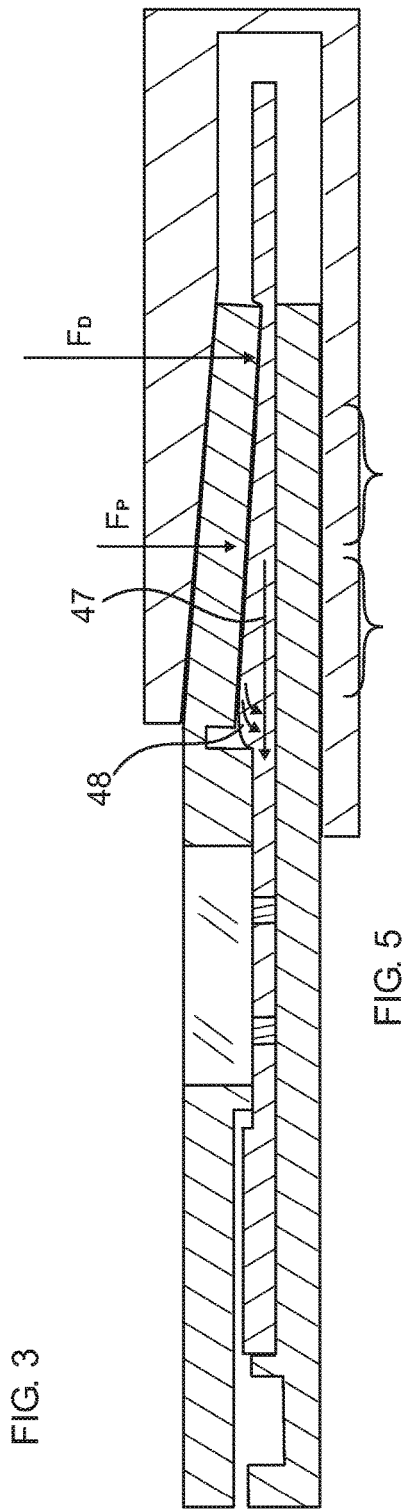

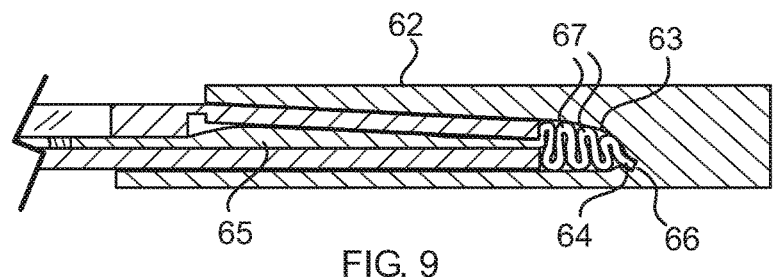
FIG. 9
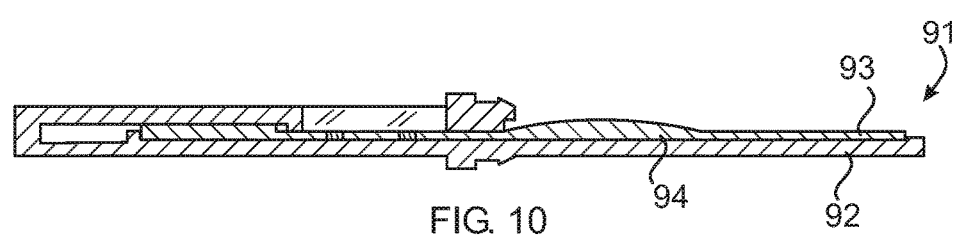
FIG. 10
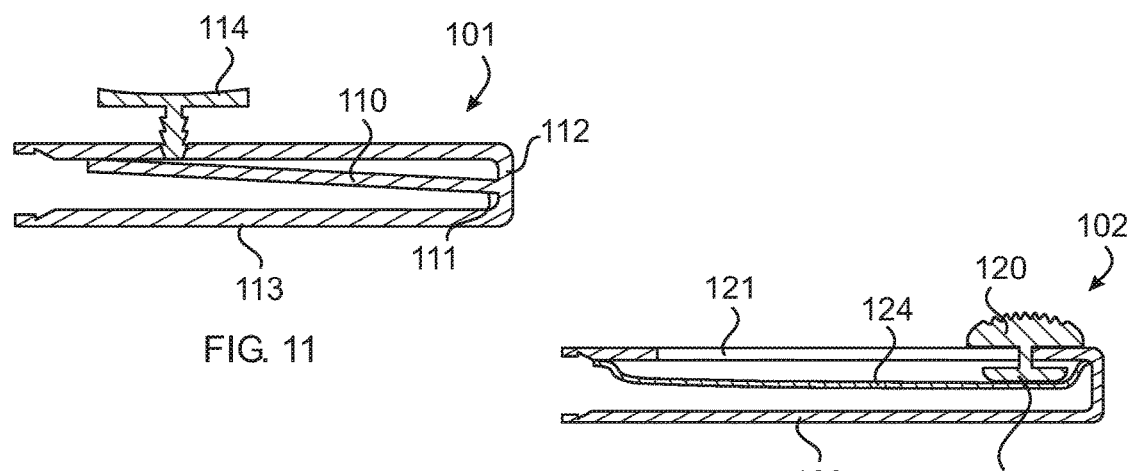
FIG. 11
FIG. 12
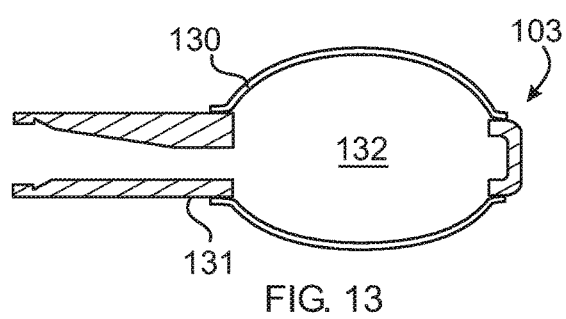
FIG. 13

RAPID DIAGNOSTIC TEST DEVICE BY DRIVEN FLOW TECHNOLOGY

BACKGROUND OF THE INVENTION

1. Field of the Invention

One or more embodiments of the invention relate generally to apparatus for analyzing liquids, such as body fluids, using labeled molecular affinity binding, such as immunochromatography. More particularly, the invention relates to strip test apparatus for detecting an analyte, such as an antibody or antigen, which may indicate a particular condition.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Labeled molecular affinity binding, such as immunochromatographic assays, have existed for decades and have proven to be an inexpensive way to screen for various conditions, such as abused drugs, and other conditions, such as pregnancy and cancer, or for single or multiple pathogenic conditions, such as HIV infection.

In the point-of-care test (POCT) setting, immunochromatographic assays are typically conducted using lateral flow strip technology as described in May et al., U.S. Pat. No. 5,656,503, incorporated herein by reference. With lateral flow devices, antibodies are movably supported on a solid support, such as a porous pad. Antigen derivatives are deposited as immobilized indicator lines downstream of the antibodies, whereby the target antigens in a fluid sample flow laterally as a liquid matrix by capillary action through the solid support. The antibodies are normally colored for visual indication. The fluid sample carries the antibodies downstream towards the indicator lines of immobilized antigen derivatives while a reaction takes place between the target antigens and the antibodies. Any antibodies that have not reacted with the antigen in the sample bind to the antigen derivatives at the indicator lines. When little or no target antigen is present in the sample, most or all of the colored antibodies are carried downstream to the indicator lines of the immobilized antigen derivatives. At the immobilized antigen derivatives, the colored antibodies bind together with the antigen derivatives in such concentrations that the colorant of the antibodies becomes readily visible. It is also known that the antigen derivatives' and the antibodies' roles can be interchanged. That is, the antigen derivatives can be labeled with colorant and movably placed in the solid support while the antibodies are placed as immobilized deposited indicator lines downstream.

Unfortunately, although they can be inexpensive and simple-to-use, depending on the type of condition being detected, these tests typically take from about 5 to 20 minutes to complete and provide a typical accuracy of between 75% and 95%, falling short of the 99% or above accuracy generally considered to be necessary for a confirmatory test. Moreover, these conventional tests provide no objective measure of a quantitative result, such as the concentration of a given drug present in the liquid being tested.

The reasons for the insufficient accuracy in many rapid in vitro diagnostic (IVD) test devices are primarily due to their current lack of overall higher sensitivity and specificity. Different samples may contain chemicals or particles which inhibit the rapid and well mixed liquid flow or otherwise interfere with one or both of the first and second affinity binding reactions.

Other prior devices have attempted to enhance sensitivity or specificity by pretreating various parts of the device with reaction or flow enhancing reagents, pH conditioning chemicals, or even non-specific adhesive blocking molecules which will "block-out" non-analyte molecules which might cause non-specific adhesion, or otherwise compete with the analyte in question for specific binding members, especially in the reaction zones region of the strip. These attempts have met with limited success in some types of testing, but do not provide the desired accuracy in many others. Also, pretreatment with two or more of the above pretreatments exacerbates the difficulties in obtaining uniform manufacturing due to potential incompatibilities between the pretreatment chemicals. For example, the pH conditioner might disrupt the effectiveness of the non-specific blocking member molecules. Moreover, the manufacturing step of pretreating with a second pretreatment chemical can dislodge some of the first pretreatment chemical.

Further, lot-to-lot variation in the manufacture of many IVD test devices can often lead to ambiguous results, such as false negatives as well as weak false positives, so-called "ghostlines" or "phantom lines". False negatives typically occur when non-specific molecules interfere with the first and/or second affinity binding actions. It has been found that non-analyte molecules can clump together in liquid samples that are not well mixed so that they temporarily prevent access between analytes and binding members. Even temporary interference in past devices can prevent an adequate number of labeled analyte complexes and/or ultimately immuno-sandwich complexes from forming. In this way, if a non-analyte molecule or clump of molecules blocks access between analytes and binding members for only a few seconds, it may be enough to induce a false negative result. Further, clumps of non-analyte molecules can carry an overabundance of the labeled mobilizable binding members to the second affinity binding site to generate a false positive result.

Lateral flow devices are useful due to their low cost and ease of use. However, prior lateral flow devices suffer from low accuracy and relatively long test wait times as detailed above. This is especially true for saliva testing because of the low concentrations of analytes present. Current lateral flow strips cannot provide the necessary sensitivity and specificity within the time normally allotted to a typical law enforcement action such as a traffic stop.

The low accuracy can be due to a number of problems unique to lateral flow-type tests. First, there is often uneven movement of the immunoparticles within the nitrocellulose membrane. Smaller, non-analyte molecules mix together with the larger analyte molecules and compete for sites, often preventing the larger molecules from reacting in the desired fashion.

Therefore, there is a need to improve the accuracy of rapid IVD test devices so that rapid, inexpensive, easily conducted and quantitative immunological testing becomes a reality.

SUMMARY OF THE INVENTION

Embodiments of the present invention provide a device for testing a liquid sample for the concentration of at least one analyte, comprising a top member; a bottom member connecting to the top member forming an internal cavity therein; a fluid directing channel formed in the internal cavity; an inlet formed in a first end of the device, the inlet fluidly communicating with the fluid directing channel; a press pad formed in the top member, the press pad configured to press against a conjugate color pad of a test strip disposed within the internal cavity; and a cap fitting over the first end of the device, the cap configured to press against a fluid collector having the liquid sample disposed therein, thereby driving the fluid sample into the fluid directing channel.

Embodiments of the present invention further provide a test system for testing a liquid sample for the concentration of at least one analyte comprising at least one test strip comprising a conjugate color pad including a source of mobilizable labeled first affinity binding members bindable to the analyte; a liquid permeable reaction region including at least one strip line including immobilized second affinity capture binding members bindable to said analyte; and a strip press pad disposed over the conjugate color pad; and a test device comprising a top member; a bottom member connecting to the top member forming an internal cavity therein; a fluid directing channel formed in the internal cavity containing the test strip; an inlet formed in a first end of the device, the inlet fluidly communicating with the fluid directing channel; a press pad formed in the top member, the press pad configured to press against the strip press pad and the conjugate color pad of the test strip; and a cap fitting over the first end of the device, the cap configured to press against a fluid collector having the liquid sample disposed therein, thereby driving the fluid sample into the fluid directing channel.

Embodiments of the present invention also provide a method for testing for an analyte in a sample, comprising disposing at least one test strip into an internal cavity formed between a top member and a bottom member of a test device; sliding a cap onto a first end of the test device to compress a fluid collector to cause the sample to be expelled from the fluid collector into a fluid directing channel formed in the internal cavity; directing the fluid from the fluid directing channel to a conjugate color pad of the test strip, the conjugate color pad disposed on a press pad of the top member; and exerting an additional force on the conjugate color pad of the test strip as the cap is slid further onto the first end of the test device.

In some embodiments, the results can be rapid qualitative/quantitative results with up to 99% accuracy.

In some embodiments, the structure of the rapid diagnostic test device causes a high speed, rapid flow of liquid out of a fluid collector toward a reaction region of the test strip.

In some embodiments, there is provided a labeled molecular affinity binding assay strip device having a source of mobilizable first affinity binding members in the conjugate color pad and a number of fixed second affinity binding sites in the reaction region of the test strip, where the reaction region is visible through a result window of the test device.

In some embodiments, the diagnostic test device provides a more predictable rate of uptake of labeled analytes at the strip lines in order to provide a quantitative result.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

FIG. 2 is a diagrammatical cross-sectional side view of the assay cartridge of FIG. 1 taken along line 2-2 shown in the cap open position;

FIG. 3 is a diagrammatical cross-sectional side view of the assay cartridge of FIG. 2 taken along line 3-3 showing the strip-enclosing constriction structure;

FIG. 4 is a diagrammatical cross-sectional side view of the strip of FIG. 2;

FIG. 5 is a diagrammatical cross-sectional side view of the assay cartridge of FIG. 1 shown in the cap closed position;

FIG. 9 is a diagrammatical cross-sectional side view of an alternate embodiment of a cap having a strip crumpling structure;

FIG. 10 is a diagrammatical cross-sectional side view of an alternate embodiment of a cartridge having a support shelf for supporting the free end of the strip;

FIG. 11 is a diagrammatical cross-sectional side view of an alternate embodiment of a cap having an internal deflectable beam progressive compression structure;

FIG. 12 is a diagrammatical cross-sectional side view of an alternate embodiment of a cap having an internal slider progressive compression structure;

FIG. 13 is a diagrammatical cross-sectional side view of an alternate embodiment of a cap having a pressurizing collapsible bulb progressive compression structure;

Figure 1:
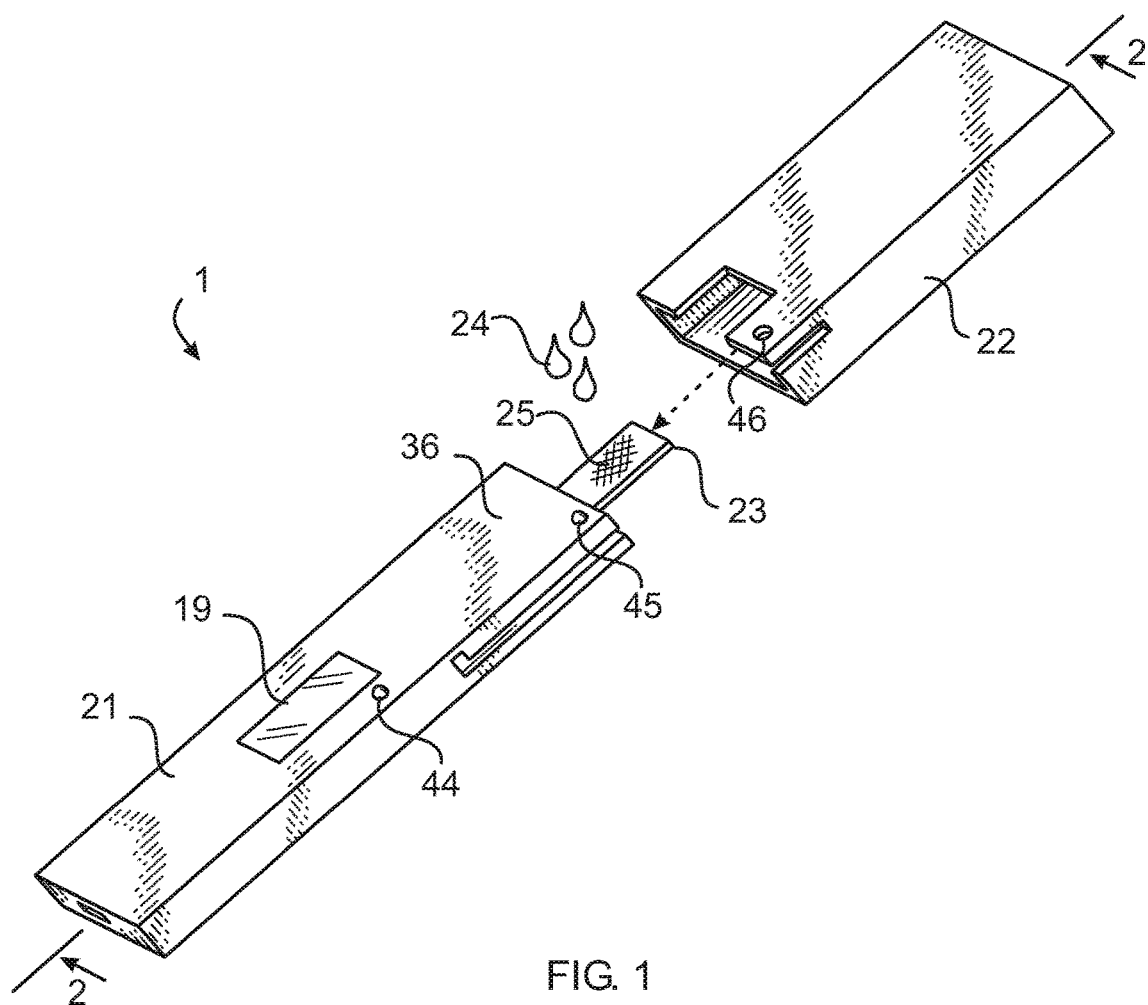
FIG. 1 is a diagrammatical perspective view of an assay cartridge according to an exemplary embodiment of the invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

As is well known to those skilled in the art, many careful considerations and compromises typically must be made when designing for the optimal configuration of a commercial implementation of any device, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

The instant embodiments are useful to rapidly determine the presence of an analyte in a liquid sample at a concentration which confirms the condition being tested. The sample can include, for example, body fluids, such as whole blood, serum, plasma, urine, spinal fluid, amniotic fluid, mucous, saliva, and the like, or other fluids used in certain food and environmental testing.

As used herein, the term "analyte" refers to a compound or composition to be measured. The analyte can be any substance, such as an antigen or ligand, for which there exists a naturally or genetically occurring specific binding member, for instance, a binding molecule such as an antibody or receptor, and other molecules that exhibit the so-called "lock-in-key" pairing function.

Analytes also includes any antigenic substances, haptens, antibodies, and combinations thereof. The analyte can include a protein; a peptide; an amino acid; a ligand; a hormone; asteroid; a vitamin; a drug, including those administered for therapeutic purposes as well as those administered for illicit purposes; a pathogen; and an exogenious infectious microbe, such as a bacterium, a virus, and metabolites of or antibodies to any of the above substances. The analyte can also comprise an antigenic marker or antibody or receptor.

The precise nature of a number of analytes, together with a number of examples thereof are disclosed in Litman, et al., U.S. Pat. No. 4,299,916, issued Nov. 10, 1981; and Tom, et al., U.S. Pat. No. 4,366,241, issued Dec. 28, 1982, each of which are herein incorporated by reference in their entirety. Certain improved accuracy devices are disclosed in U.S. Pat. No. 8,021,625 (Wang et al.), which is incorporated herein by reference in its entirety.

The signal provided to the user of the device is provided by accumulation of a visually detectable label conjugated to a mobilizable binding member such as a specific antibody and/or antigen; ligand and/or receptor. This mobilizable binding member is sometimes referred to as a "binding member molecule", "a first affinity binding member", "labeled binding member" or simply "conjugate". In the instant embodiments, labels that produce a readily detectable signal are used. Thus, the instant embodiments provide colored labels which permit visible detection of the assay results without the addition of further substances and/or without the aid of instrumentation. However, in some embodiments, instrumentation may be used to provide a comparative or quantitative representation of the concentration of analyte in the sample.

The test strips described in these embodiments can include regions or pads that may include a dry, porous material. By "porous" it is meant that the matrix of material forming the porous structure allows liquids to flow through it.

As used herein, the term "sample pad" or "fluid collector" means the part of the assay device which is in direct contact with the liquid sample first during test operation, i.e., it receives the sample to be tested for the analyte in question. The fluid collector may be made of porous material, such as porous paper, cotton, cellulose, mixed fibers, glass fiber, polyester fiber, and the like.

The term "conjugate pad" or "conjugate color pad", as used herein, refers to the part of the assay device which is in liquid flow contact with the porous material of fluid collector. The contact can be an overlap or end-to-end connection, such that the liquid sample can migrate via wicking action or by surface tension-based forces such as capillary forces from the fluid collector through the conjugate pad. The conjugate pad comprises a porous material and a mobilizable labeled reagent that is capable of binding the analyte in question to form a labeled reagent-analyte complex which then migrates via liquid flow with the liquid sample along the pad.

The term "mobilizable" as referred to herein means diffusively or non-diffusively attached, or impregnated. The mobilizable reagents are capable of dispersing with the liquid sample and carried by the liquid sample in the liquid flow.

In one exemplary embodiment, human immunodeficiency virus ("HIV") in a fluid specimen, such as saliva, is detected as a putative target analyte. Those skilled in the art will readily appreciate adaptation of these embodiments to detect other analytes indicative of other pathogens, or pathogenic conditions in body, drugs of abuse ("DOA"), food or environmental fluid specimens, and the like.

Further the exemplary embodiments will be described in connection with an immunochromatographic assay based on antigen/antibody binding. Those skilled in the art will readily appreciate adaptation of these embodiments to other types of molecular affinity binding-based tests.

Referring now to FIGS. 1-5, there is shown a diagrammatical illustration of a labeled molecular affinity binding test device 1 including a cartridge body 21 and a cap 22 made from a generally liquid impermeable durable material such as injection molded plastic. The cartridge carries in an internal cavity at least one test strip 23 containing the chemicals necessary to conduct the labeled molecular affinity binding test. The strip has an oblong backing 15 made from liquid impermeable material such as plastic extending the entire length of the strip so that liquid can ride along the upper surface of the backing during its flow. The internal cavity of the cartridge body is shaped and dimensioned to carry a first portion 17 of the strip including the conjugate pad 26 impregnated with a lyophized, mobilizable, first affinity binding member, such as an HIV antigen or antibody, conjugated to a label such as colloidal gold, and a reaction region 27 including one or more zones 28,29 impregnated with lyophized, immobilized, second affinity binder members intended to capture first affinity bound molecules. Thus the first affinity binding members are initially separated from the second affinity binding members.

The cap 22 can be shaped and dimensioned to engage the cartridge body, and have an internal chamber shaped and dimensioned to enclose a second, remainder portion 16 of the strip including the exposed end of the sample pad 25.

The device can be delivered in a pre-used condition where the strip has been preloaded into the cartridge and the cap protectively placed over the free end of the strip and held in place by a nib 45 on the cartridge engaging a hole 46 in the cap.

To initiate a test, the user removes the cap 22 so that the device is in the cap open position as shown in FIG. 1, and deposits a liquid sample 24 upon the sample pad 25 at a distal exposed end of the strip 23. The sample liquid then flows primarily through the forces of capillarity and gravity into a thickened, convexly-shaped conjugate pad 26. The liquid will tend toward fully saturating the thickened conjugate pad before any substantial flow leaves the conjugate pad for the reaction region 27.

The thickened conjugate pad 26 is located beneath a compression structure 36 on the cartridge body 21. The compression structure can be formed by a cantilevered beam 38 having a fixed proximal end and a distal free end 42. The beam is allowed to deflect downwardly as it comes into contact with the sloped surface of the ramp 32. The downward deflection is facilitated by a narrow isthmus of material 37 connecting the fixed proximal end of the beam to the cartridge body. The isthmus acts as a relatively stiff mechanical hinge, providing predetermined resistance to deflection which can be selected during manufacture by selecting the thickness of the isthmus. This helps the beam from being inadvertently deflected prior to the directed intentional placement of the cap.

The user then replaces the cap 22 and forces it into the cap closed, test initiation position shown in FIG. 5. A second nib 45 engages the hole 46 on the cap to indicate that the cap has reached the closed position. The sloped surface of the ramp 32 of the cap having an angle 33 of between about 0 and 25 degrees progressively forces the cantilevered beam of the compression structure 36 downward as the cap moves toward the closed position. The beam presses against the top side of the thickened conjugate pad 26 forcing liquid out of the pad due to an overpressure force an on downstream as indicated by the arrow 47 toward the reaction region 27 carrying one or more result zones 28,29 of immobilized, second affinity binding members. The analyte molecules already bound to conjugated first affinity binding members can now bind to the immobilized members located in the zones and accumulate there in significant numbers to indicate a test result through the observation window 19.

Liquid continues to flow into an absorbent reservoir pad 30 located at the proximal end of the cartridge. An empty chamber 31 having an opening 39 outside the cartridge at the proximal end of the cartridge relieves any buildup of backwards pressure against the flow of liquid into the reservoir. Optionally, the chamber can have an opening to the outside to ensure no buildup of pressure occurs during the movement of liquid through the device. Optionally, an amount of desiccant can be placed in the chamber to keep the strip dry until use.

As shown in FIG. 3, it is important to note that the reaction region 27 part of the strip 23 is surrounded on its perimeter 35 by a strip-enclosing constriction structure formed by the close proximity of the cartridge body 21 so that once liquid has reached the reservoir 30, additional liquid is drawn out of the conjugate pad by siphoning forces in combination with the other forces. This siphoning force takes over for a diminishing compression force as the beam reaches its full deflection, so that the pressure of the liquid flow is maintained. The sample pad, conjugate pad, reaction region, and absorption pad are in direct liquid flow contact with each other such that the direction of liquid flow in the test device is from the sample pad to conjugate pad to reaction region and ultimately to the absorption pad. Thus, the liquid sample is driven through the strip by a force which is the combination of forces due primarily to compression forces and siphoning, and potentially gravity.

Figure 6:
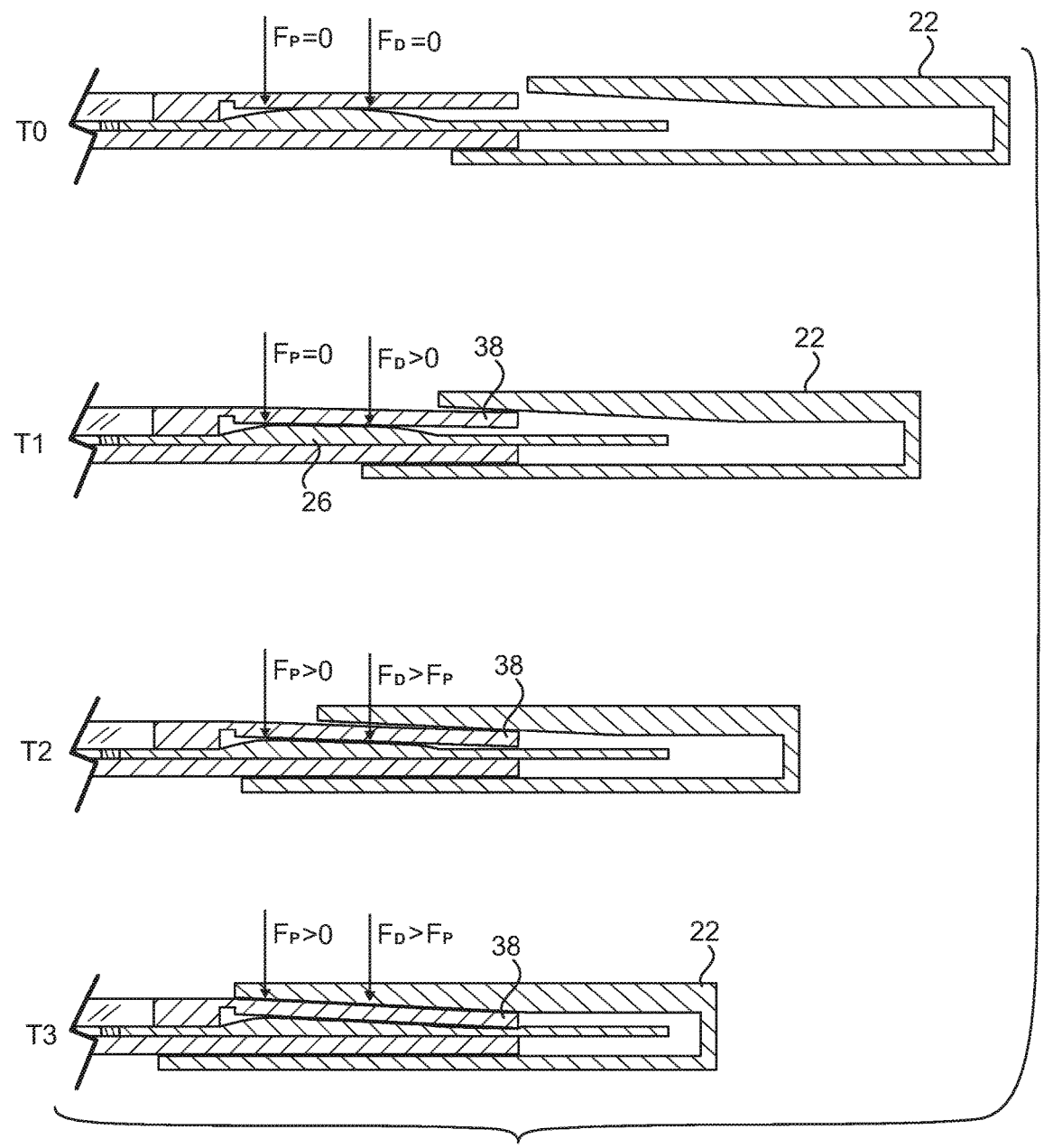
FIG. 6 is a diagrammatical cross-sectional side view of the cartridge of FIG. 1 showing progressive compression force components at various times and position during cap emplacement.
Figure 7:
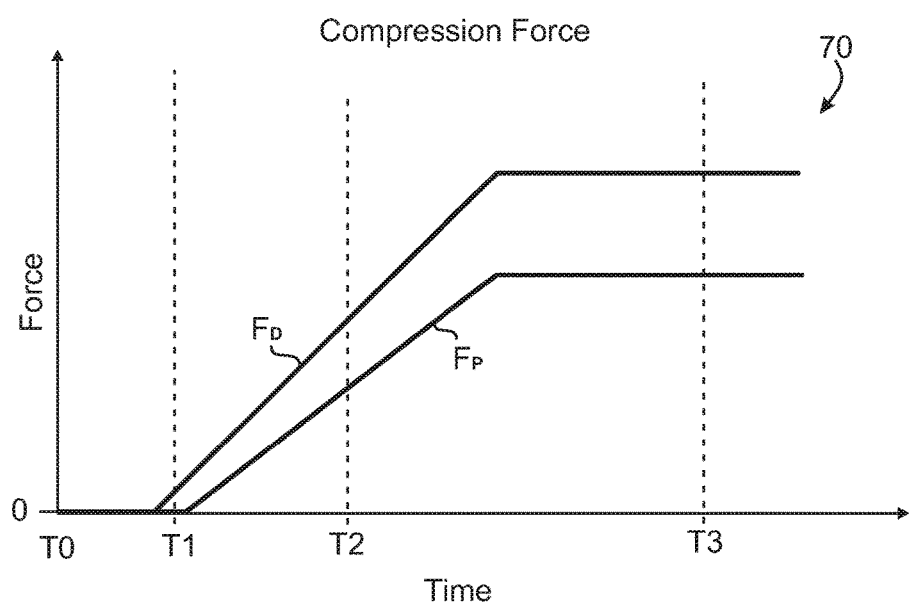
FIG. 7 is a diagrammatical chart showing progressive compression force components at various times during cap emplacement.

As shown schematically in FIG. 6 and graphically in FIG. 7, the compression force 70 is applied progressively along the downstream direction 47 of liquid flow during cap emplacement onto the cartridge body. Before the cap 22 contacts the cartridge body 21 at T0 there is no compression force applied. At time T1, when the cap 22 has been moved more proximally, the deflecting the beam 38 generates a compression force having a force component Fd applied to a distal point on the conjugate pad 26 that is greater than zero while the force component Fp at a proximal point remains zero. At time T2, as the compression structure beam 38 becomes more deflected, a compression force is applied having a force component Fp applied to the proximal point on the conjugate pad 26 that is greater than zero, while the force component Fd at the distal point is greater than Fp. At time T3 when the compression structure beam 38 is fully deflected and the cap 22 is in the closed position, a compression force is applied having a force component Fp and Fd at their maximums, where distal point Fd remains greater than Fp.

Figure 8:
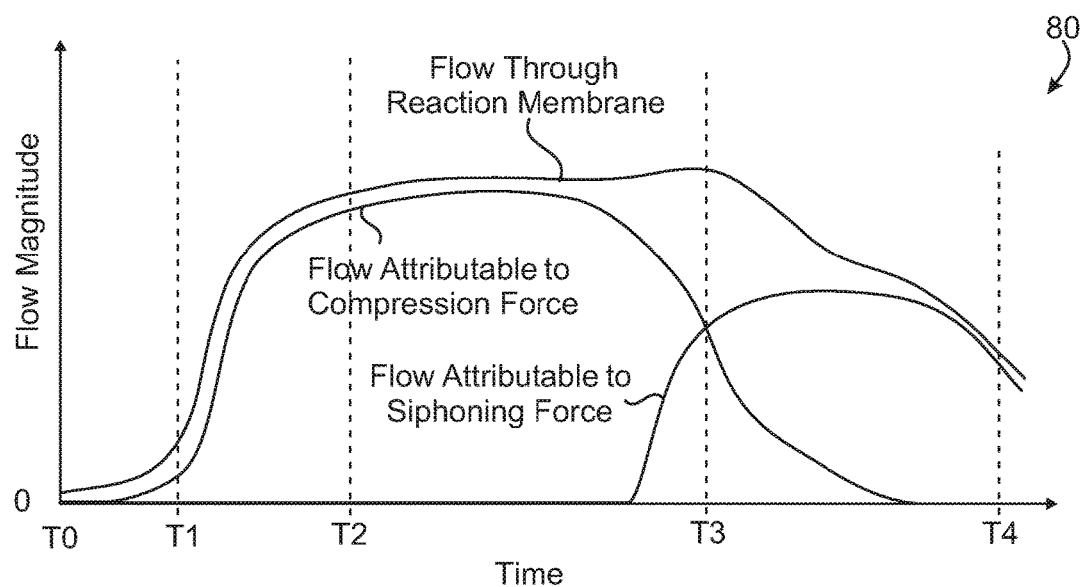
FIG. 8 is a diagrammatical chart showing the relatively uniform flow magnitude during a transition from primarily a compression driving force to a siphoning driving force.

As graphically shown in FIG. 8, the magnitude of the flow through the reaction region over time 80 is at T0 first attributable to surface tension forces (also known as capillarity) alone while the cap remains in the open position. Then as the cap is replaced from T1 to T3 the overall flow through the reaction region is primarily attributable to the compression force. After the cap has been replaced, the flow attributable to the compression force drops off, while the flow attributable to siphoning increases. By T4, the flow is almost entirely driven by siphoning. In this way, the magnitude of the flow through the reaction region is more uniform over a longer period of time because the flow occurs primarily due to overpressure forces during a first time period, and primarily due to siphoning forces during a second, subsequent time period.

Referring now to FIG. 9 there is shown an alternate embodiment of the progressive compression structure. The cap 62 similar to the device of FIG. 1 includes an additional angled bulkhead 63 for directing the distal end 64 of the strip 65 toward a receptacle 66 as the cap is moved from the open position to the closed position. Once the distal end of the strip is trapped in the receptacle, the bulkhead forces the end of the strip crumple upon itself into corrugations 67 which serve to drive liquid out of the sample pad and downstream into the conjugate pad. This added source of liquid can further pressurize the liquid exiting the conjugate pad. The strip crumpling structure can be used alone or in combination with other structures for driving liquid in a downstream direction on the strip.

Referring now to FIG. 10 there is shown an alternate embodiment of the cartridge body 91 having a support shelf 92 supporting the distal end 93 of the strip 94. Further, the top of the conjugate pad 95 is exposed. This cartridge body can be used with various progressive compression structures as detailed below.

In FIG. 11 there is shown an alternate embodiment of the progressive compression structure 101 having a deflectable beam 110 having a fixed end 111 secured to the distal end 112 of the cap 113. Once the cap is place in a closed position upon the cartridge body 91, the beam is located above the sample pad and the conjugate pad. Upon depressing a push button 114, the beam is deflected against the sample pad and the conjugate pad in a progressive compression action which forces liquid from the sample pad and conjugate pad toward the reaction region.

In FIG. 12 there is shown an alternate embodiment of the progressive compression structure 102 having a moveable slider 120 mounted within a track 121 on the cap 122. The slider has a shoe 123 which bears against the sample pad once the cap is placed in a closed position upon the cartridge body 91. Upon pushing the button of the slider proximally toward the proximal end of the cartridge, the shoe progressively imparts a compression force along the sample pad and then the conjugate pad of the strip which forces liquid from the sample pad and conjugate pad toward the reaction region. A protective, friction-reducing bib 124 made from a flexible liquid resistant material such as a pliable plastic separates the bottom of the shoe from the strip and facilitates the sliding of the shoe over the strip.

In FIG. 13 there is shown an alternate embodiment of the progressive compression structure 103 having a pressure inducing collapsible bulb 130 made from resiliently flexible, air-tight material such as rubberized plastic formed into the cap 131. Once the cap is placed in a closed position upon the cartridge body 91, an air-tight seal is formed with the cartridge body over the end of the strip and the air-filled chamber 132 inside the bulb is open to the end of the strip. The bulb can then be collapsed under the force of a person's finger and thumb to increase the pressure within the chamber imparting a force progressively from the exposed end of the strip at the sample pad and then on to the conjugate pad which forces liquid from the sample pad and conjugate pad toward the reaction region.

The application of the progressive compression force has a dramatic effect on micro-flow dynamics in the strip. In general, the result is a more rapid and thorough mixing of the sample with the reaction molecules so that a greater and more rapid opportunity is provided for the first and second bindings to occur, and a more even liquid front reaching the sites of second affinity binding.

More specifically, the pressurized movement of the liquid sample through the porous material of the conjugate pad 26 causes the liquid front to separate into branches and rejoin from different directions as it courses around the material fibers. The convergence from different directions causes a mixing across the liquid front and the liquid that follows as the sample flows downstream 47. This enhanced mixing can cause the break-up of clumps of non-analyte molecules which may carry mobilizable labeled binding members, to reduce false positives. The mixing also reduces the differences in the concentrations of non-analyte molecules and labeled analyte complexes so that they are spread more evenly.

In addition, prior to the compression force being applied, the liquid has tended to saturate the thickened conjugate pad 26. Once the compression force is applied, the liquid forcefully exits the conjugate pad into a narrower cross-section of the strip entering the reaction region 27. This action increases the velocity of the liquid in the reaction region according to the Bernoulli Principle, reducing its pressure causing further mixing and leading to a more evenly mixed liquid front. Further, because of the thickened shape of the conjugate pad, the direction of flow of the liquid exiting the upper parts of the conjugate pad must make a downward turn 48 to flow into the reaction region. This change in direction also serves to better mix the liquid.

Once the liquid front reaches the reaction region 27, the concentrations have superior uniformity across the width of the strip which leads directly to giving the labeled analyte complexes a greater opportunity to form the second affinity binding at the immobilized sites in the result zones 28,29 and thereby increasing the overall sensitivity and specificity of the test and reducing false negatives.

Figure 14:
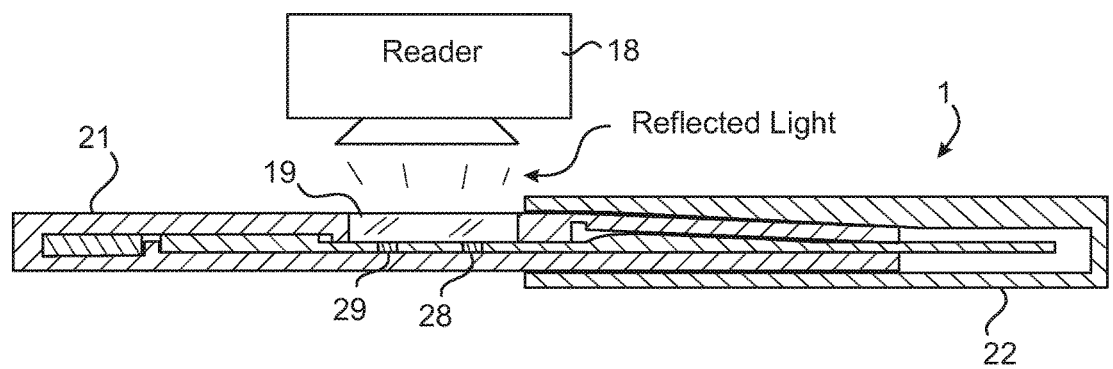
FIG. 14 is a diagrammatical cross-sectional side view of the cartridge of FIG. 1 loaded in a result reader.

Within 10 seconds or less a predicable amount of reactable sample liquid has passed through the conjugate pad and through the reaction region. This amount is about 100 to 300 microliter. As shown in FIG. 14, an automated reader 18 can read by reflected light the result of the test and generate an electronic signal that can be forwarded to a computer for further analysis and distribution to a data network. The computer can be implemented using a mobile phone device running the appropriate software, for example. By being able to predict the amount of reacted sample that has passed through the reaction region, the intensity of the lines in the result zones can indicate a quantitative result. In other words, the automated reader can the detect not just whether a line has appeared or not, but rather the intensity of the line, and digitize that intensity reading. That reading corresponds directly with the amount of analyte present in the sample, providing a digitized quantitative result.

Figure 15:
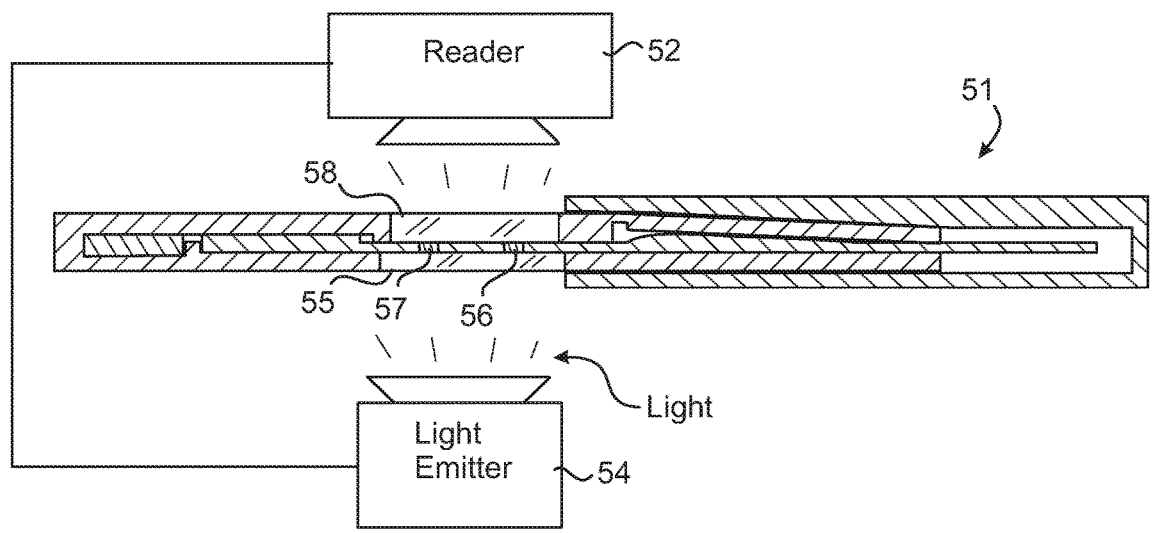
FIG. 15 is a diagrammatical cross-sectional side view of an assay cartridge according to an alternate exemplary embodiment of the invention having a light emitter enhanced reader.

Alternately, as shown in FIG. 15, a device 51 can include a second window 55 located beneath the result zones 56,57 so that a light emitter 54 can shine light through the reaction region to be received by the reader 52 and the mobile phone analysis tool 53. Indeed, the entire cartridge can be made from translucent material.

Figure 16:
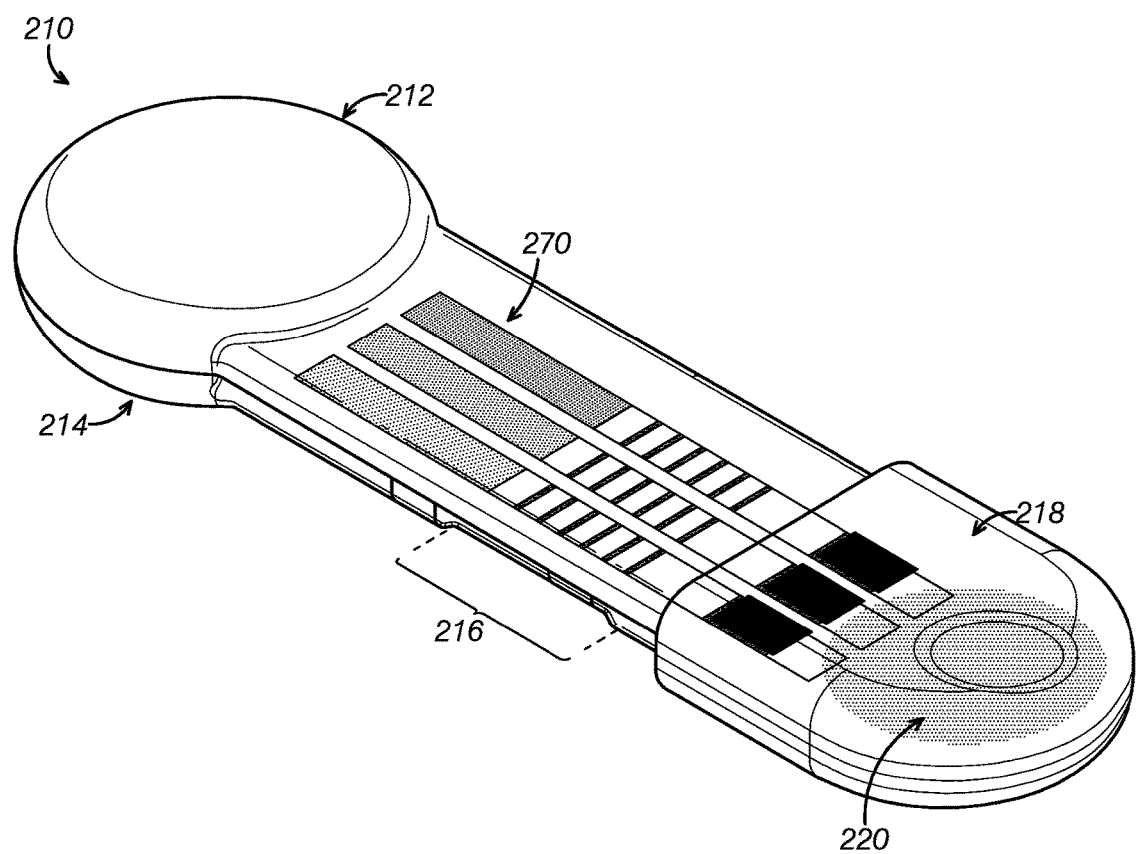
FIG. 16 illustrates a partially transparent perspective view of a rapid diagnostic test device, having three test strips and a fluid collector disposed therein, in accordance with an embodiment of the present invention.
Figure 22:
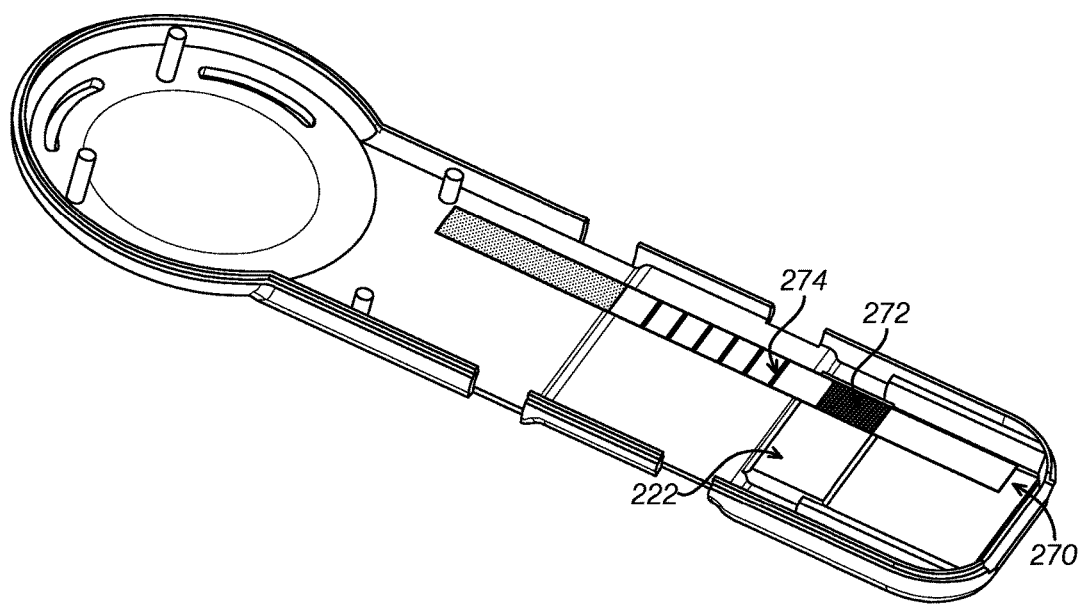
FIG. 22 illustrates a perspective view of the top member of FIG. 17A with a test strip disposed therein.

According to an exemplary embodiment of a driven flow test device and referring to FIG. 16, a rapid diagnostic test device 210, also referred to as simply test device 210, can include a top member 212 connected to a bottom member 214. One or more test strips 270 (three such test strips 270 are shown in FIG. 16) may be disposed inside the test device 210 between the top member 212 and the bottom member 214. A result window 216 may be formed in at least one of the top member 212 and the bottom member 214 to allow a user to view the results of the test. As described in greater detail below, the result window 216 can align with one or more strip lines 274 (see FIG. 22) of the test strip 270.

Figure 21:
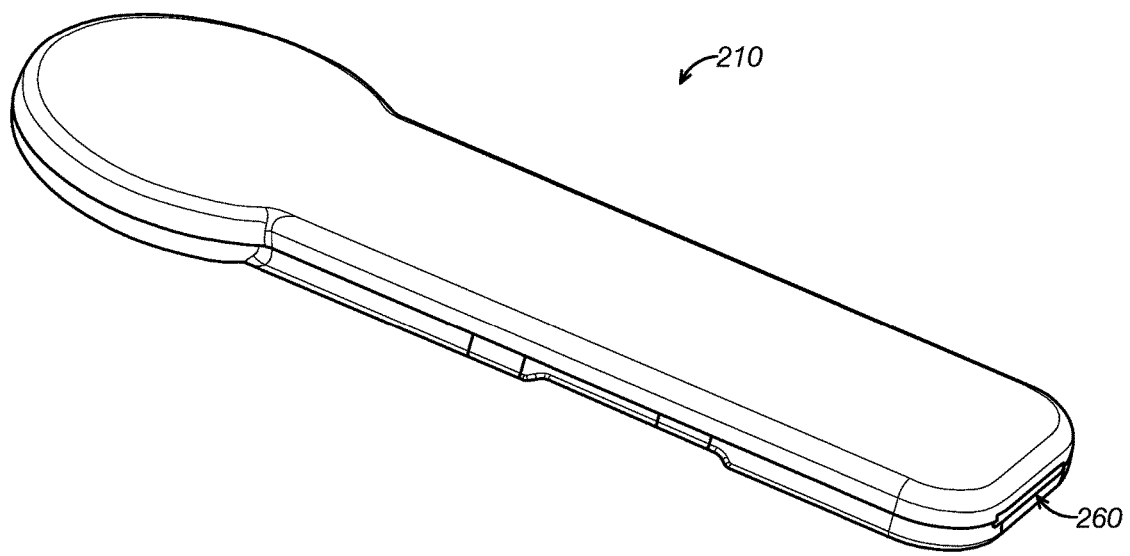
FIG. 21 illustrates a partially transparent perspective view of the rapid diagnostic test device of FIG. 16, without test strips or a fluid collector and cap disposed therein.

A cap 218 may be slidably and removably disposed on one end of the test device 210. During use of the test device 210 to test a sample for an analyte, the cap 218 is slid onto the end of the test device 210 and a fluid collector 220, disposed within and extending from an inlet 260 (see FIG. 21) of the test device 210, may be compressed to drive sample fluid onto and through the test strips 270, as described in greater detail below.

Figure 17A:
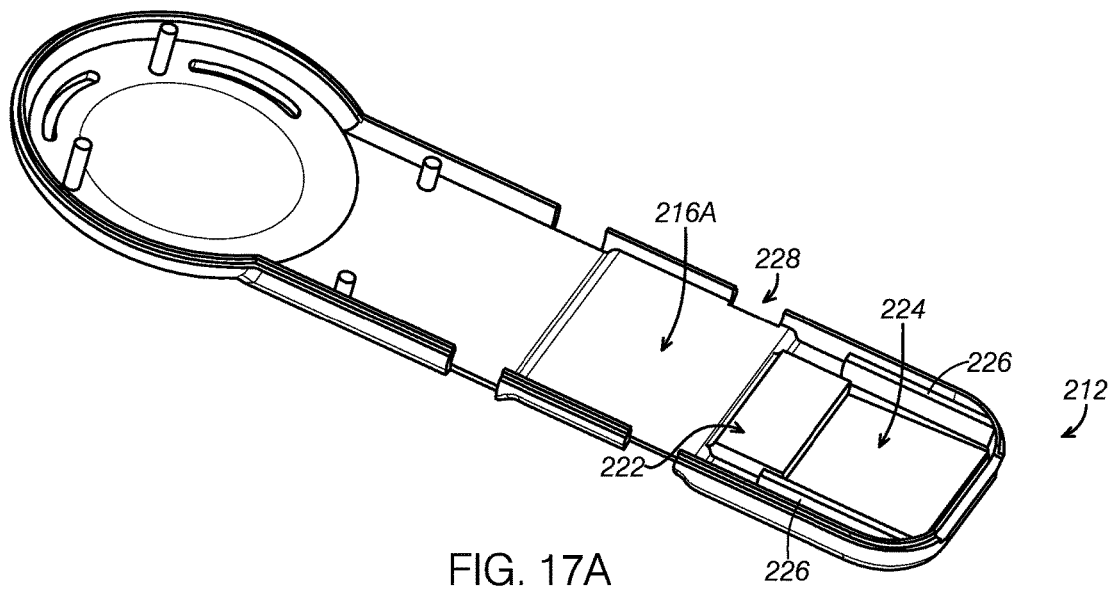
FIG. 17A illustrates a front perspective view of a top member of the rapid diagnostic test device of FIG. 16.
Figure 17B:
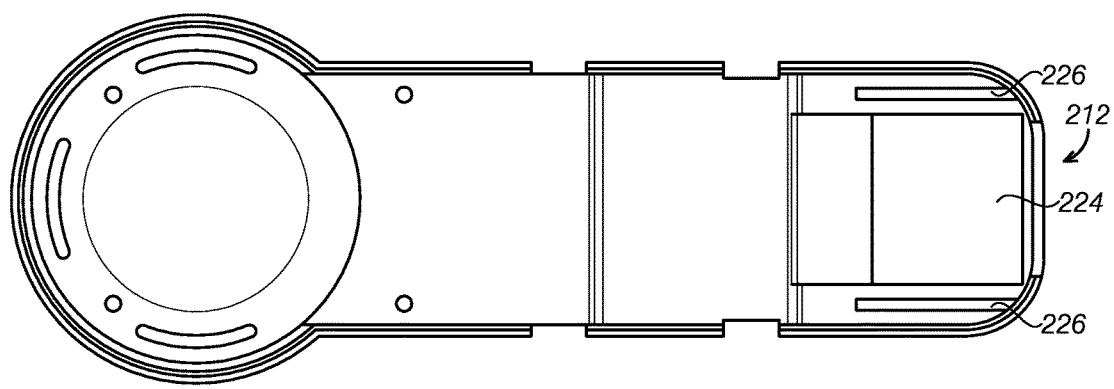
FIG. 17B illustrates a front view of the top member of the rapid diagnostic test device of FIG. 16.
Figure 17C:
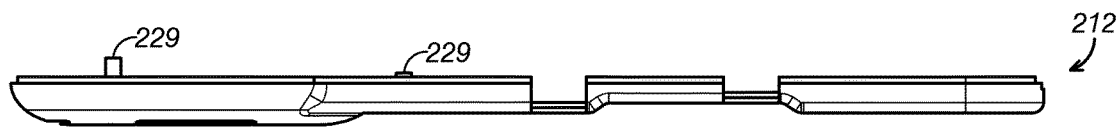
FIG. 17C illustrates a side view of the top member of the rapid diagnostic test device of FIG. 16.
Figure 23:
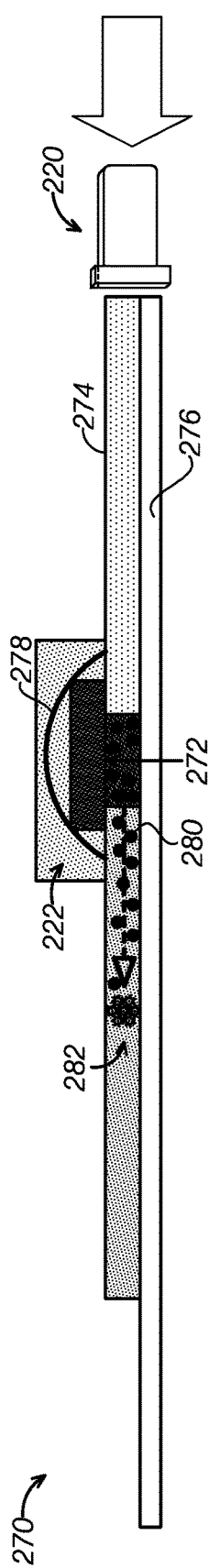
FIG. 23 illustrates a side view of an exemplary test strip, demonstrating fluid movement therealong.

Referring now to FIGS. 17A, 17B and 17C, the top member 212 is shown in detail, without the bottom member 214 attached thereto. The top member 222 can include a press pad 222 adapted to align with a conjugate color pad 272 and strip press pad 278 of the test strip 270 (see FIG. 23). A fluid directing channel 224 is formed at one end of the top member 212. The fluid directing channel 224 is bounded on each side by side walls 226 and terminates at the press pad 222. As discussed below, the fluid directing channel 224 may direct fluid from the fluid collector 220 toward the conjugate color pad 272 of the test strip 270.

A top member result window 216A may be disposed in the top member 212. The top member result window 216A may be formed from a clear or opaque material, allowing a user to read results on the test strip 270 disposed within the test device 210.

Figure 18A:
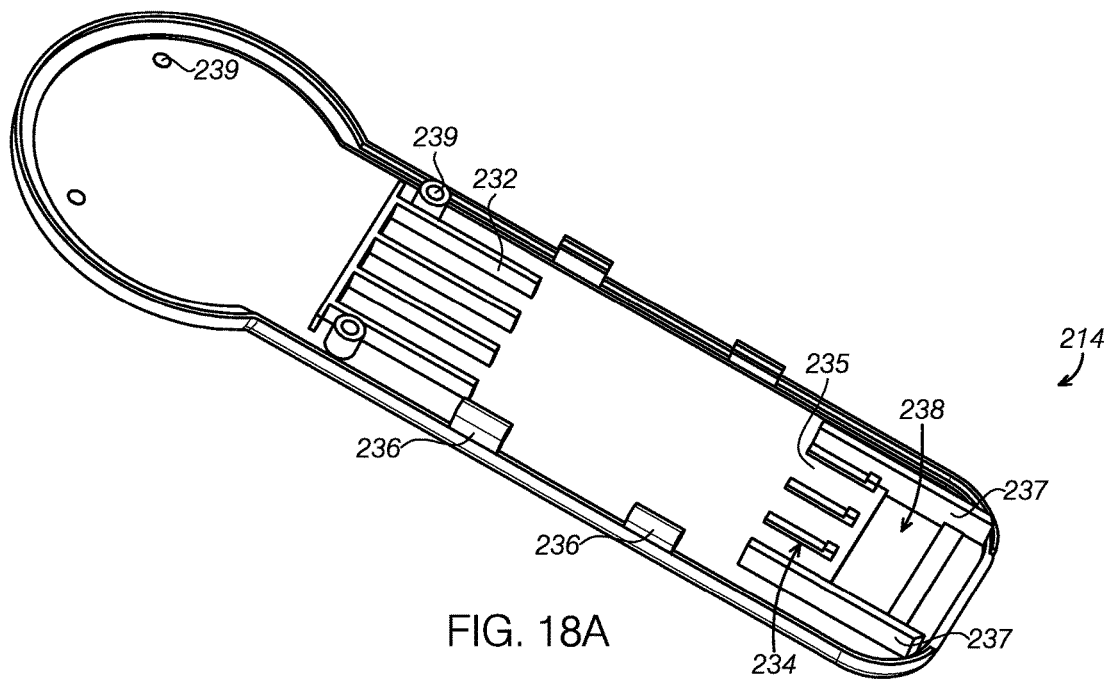
FIG. 18A illustrates a front perspective view of a bottom member of the rapid diagnostic test device of FIG. 16.
Figure 18B:
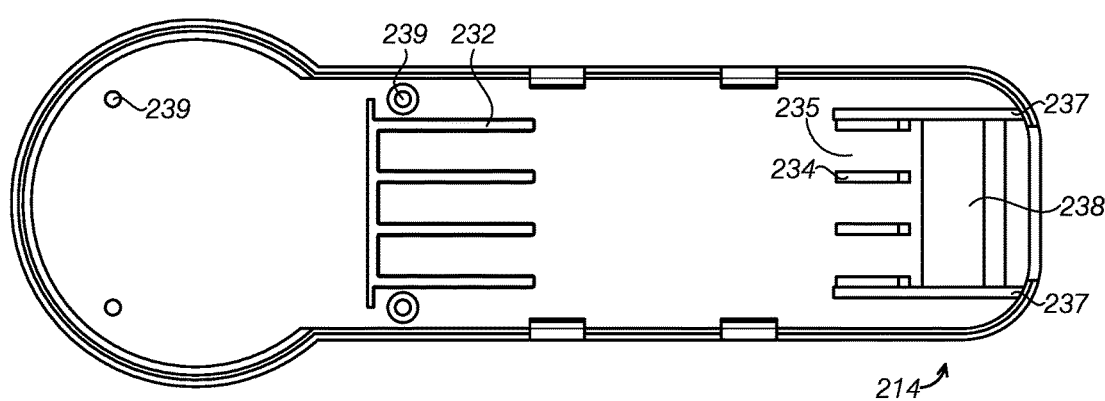
FIG. 18B illustrates a front view of the bottom member of the rapid diagnostic test device of FIG. 16.
Figure 18C:
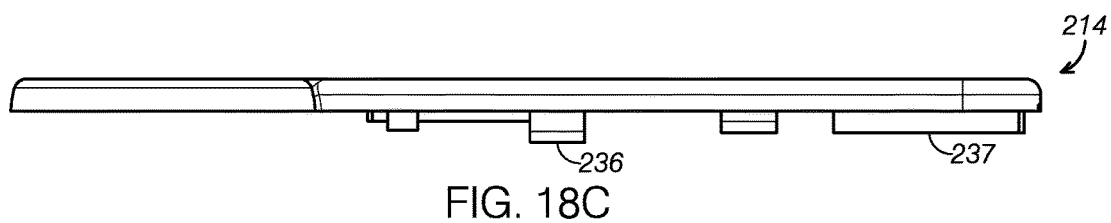
FIG. 18C illustrates a side view of the bottom member of the rapid diagnostic test device of FIG. 16.

Referring to FIGS. 18A, 18B and 18C, the bottom member 214 is shown in detail, without the top member 212 attached thereto. The bottom member 214 includes a fluid directing channel 238 that aligns with the fluid directing channel 224 of the top member 212 to receive the fluid collector 220 therein. Like the fluid directing channel 224 of the top member 212, the fluid directing channel 238 of the bottom member 214 can be bounded on each side by side walls 237.

A plurality of side bars 224 can define strip slots 235 for disposing the test strips 270. The side bars 224 may be disposed adjacent to the inner terminus of the fluid directing channel 238. Similarly, a plurality of upper side bars 232 may be disposed on an opposite end (opposite the plurality of side bars 224) of the bottom member. The plurality of upper side bars 232 may align with the plurality of side bars 224 so that the test strips 270 are disposed within the test device 210 adjacent to each other and generally parallel with each other, as shown in FIG. 16.

The bottom member 214 can include a plurality of secure/alignment holes 239 to receive secure/alignment pins 229 of the top member 212 when the top member 212 is attached to the bottom member 214. Side clips 236 may be disposed on each side of the bottom member 214. The side clips 236 may fit into connection notches 228 of the top member 212 to removably secure the top member 212 to the bottom member 214. Of course, other methods of connecting the top member 212 to the bottom member 214 are contemplated within the scope of the present invention. Such connections may include friction fit, fasteners, twist lock connectors, or the like.

Figure 19A:
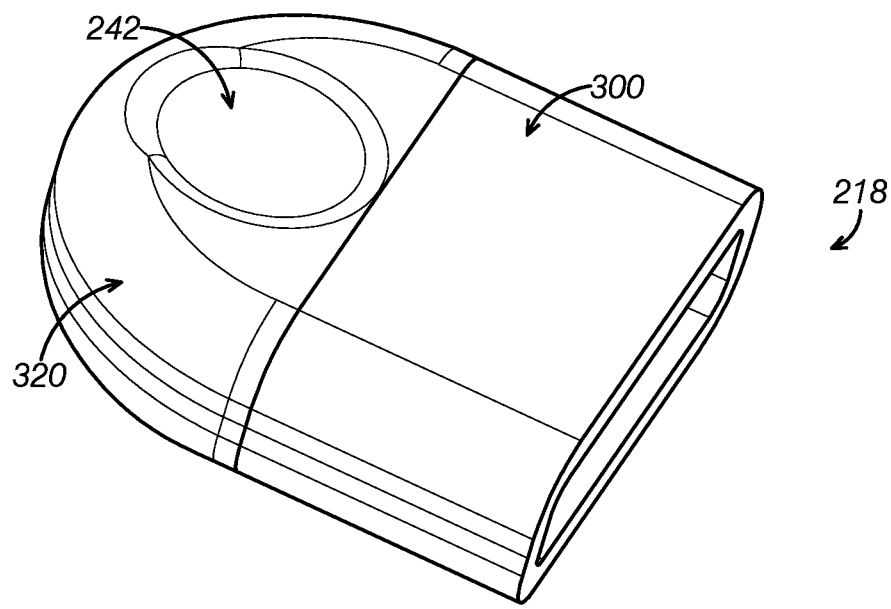
FIG. 19A illustrates a front perspective view of a cap member of the rapid diagnostic test device of FIG. 16.
Figure 19B:
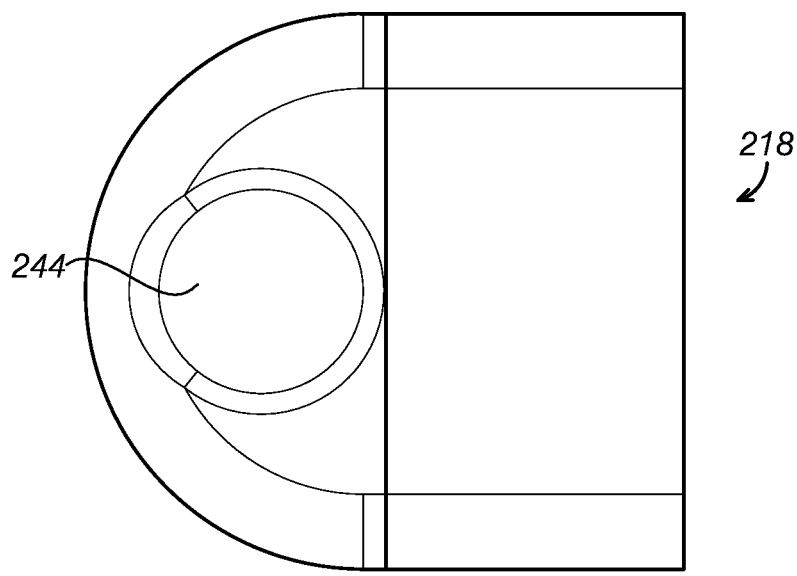
FIG. 19B illustrates a back view of the cap member of the rapid diagnostic test device of FIG. 16.

Referring to FIGS. 19A and 19B, the cap 218 is shown in greater detail. The cap 218 may be configured to fit onto the end of the test device 210 as shown in FIG. 16. A top notch plate 242 and a bottom notch plate 244 may be formed in the cap 218. The notch plates 242, 244 may be disposed directly opposite each other, as shown, or, in some embodiments, may be offset. The notch plates 242, 244 may be formed in various shapes and sizes and typically protrude into an interior region of the cap 218 to press against the fluid collector 220, as discussed in greater detail below. In some embodiments, the cap 218 may sealingly engage the top member 212 and the bottom member 214 such that excess fluid in the cap 218 may not leak out while the cap is disposed on the test device 210.

Figure 19C:
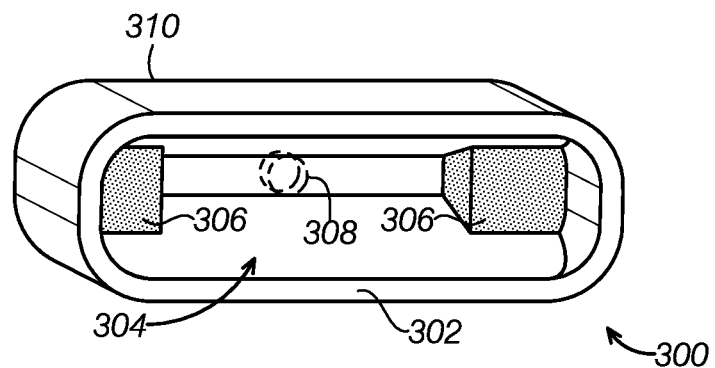
FIG. 19C illustrates a front perspective view of a squeezing portion of the cap member of FIG. 19A.
Figure 19D:
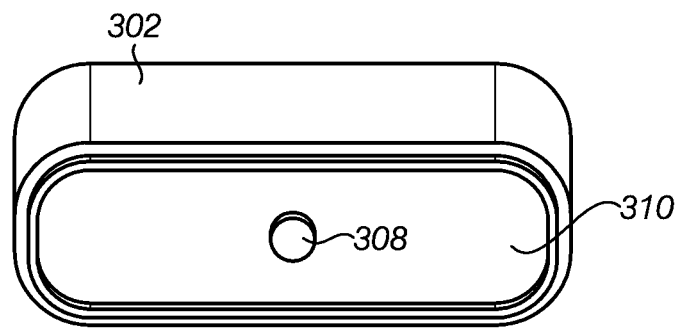
FIG. 19D illustrates a back view of the squeezing portion of FIG. 19C.
Figure 19E:
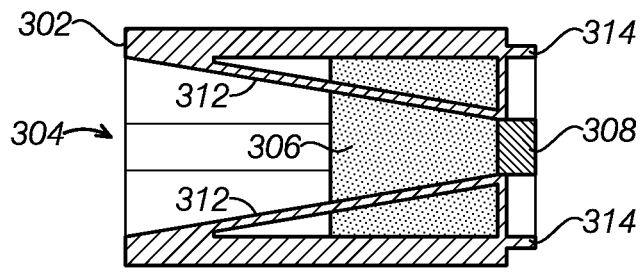
FIG. 19E illustrates a partially cut-away side view of the squeezing portion of FIG. 19C.
Figure 19F:
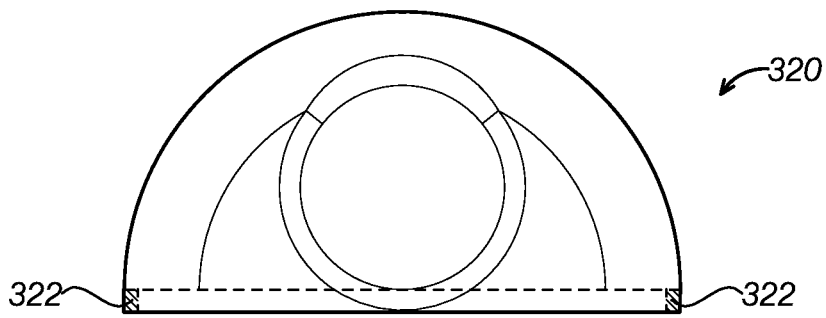
FIG. 19F illustrates a side view of a specimen collection portion of the cap member of FIG. 19A.
Figure 19G:
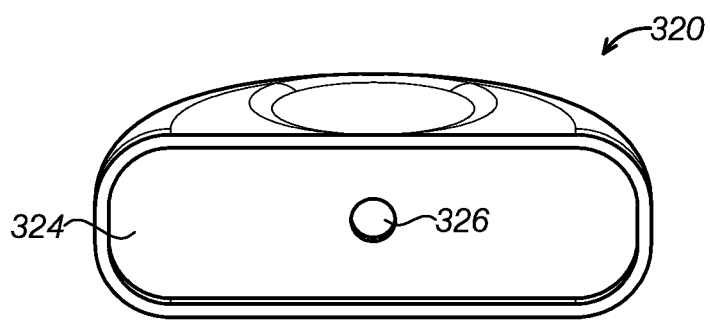
FIG. 19G illustrates a front view of the specimen collection portion of FIG. 19F.
Figure 19H:
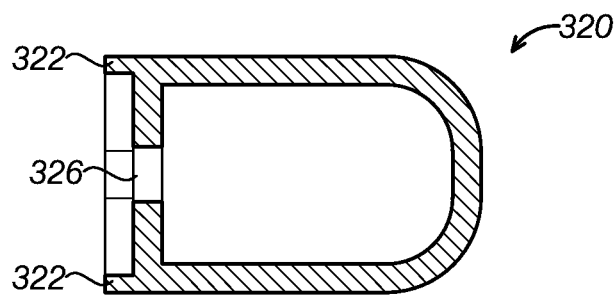
FIG. 19H illustrates a partially cut-away side view of the specimen collection portion of FIG. 19F.

In some embodiments, the cap 218 may be formed from a specimen retention portion 320 and a fluid collector squeezing portion 300 (also referred to simply as squeezing portion 300). FIGS. 19C to 19E show views of the squeezing portion 300. The squeezing portion 300 can include an outer body 302 having a fluid collector opening 304 at one end thereof. Side walls 306 may be disposed inside of the opening 304 to provide a stop against the device 210. This stopping action can help assure the user that the cap 218 is properly placed onto the device 210 before squeezing the squeezing portion 300.

A back side 310 of the squeezing portion 300 may be solid or fluid impermeable, except for a specimen collection opening 308 formed therein. When the squeezing portion 300 is squeezed, the specimen may be delivered to the device 210, as described below, while excess fluid may pass through the specimen collection opening 308 and into the specimen retention portion 320 of the cap 218. An interior of the cap 218 may be sloped on one or both sides to direct fluid to the device 210 and limit the fluid flow through the specimen collection opening 308. A ramp 312 on both sides of the cap 218 is shown in FIG. 19E. The squeezing portion 320 may be formed at least partially from a resiliently deformable material that may be squeezed together to reduce the volume inside the fluid collector opening 304.

Referring now to FIGS. 19F through 19J, the specimen retention portion 320 is shown in greater detail. The specimen retention portion 320 may include a solid front panel 324 that aligns with the back side 310 of the squeezing portion 300. A retention portion opening 326 may be formed in the front panel 324 of the specimen retention portion 320. The retention portion opening 326 may align with the specimen collection opening 308 of the squeezing portion when the cap 218 is assembled as shown in FIG. 19A. In some embodiments, the retention portion opening 326 may be formed as a one-way valve, where specimen is permitted into the specimen retention portion 320 when the specimen retention portion 320 is attached to the squeezing portion 300, but, when detached, the retention portion opening 326 may automatically seal to prevent specimen from spilling from the specimen retention portion 320.

Figure 19J:
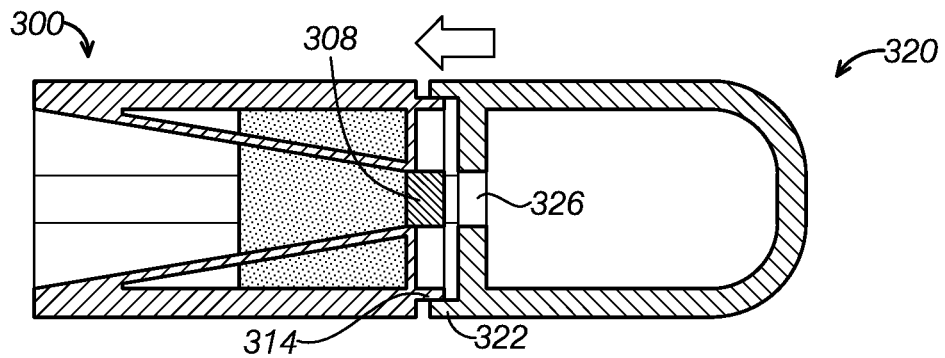
FIG. 19J illustrates a side view showing coupling of the squeezing portion of FIG. 19C with the specimen collection portion of FIG. 19F.

Alignment pins 322 may coordinate with alignment pins 314 of the squeezing portion (see FIG. 19E) when the squeezing portion 300 is assembled with the specimen retention portion 320 as shown in FIG. 19J.

In some embodiments, the specimen retention portion 320 may be formed separately from the squeezing portion 300. In other embodiments, the cap 218, including the specimen retention portion 320 and the squeezing portion 300 may be formed integrally, as a single component.

Figure 20:
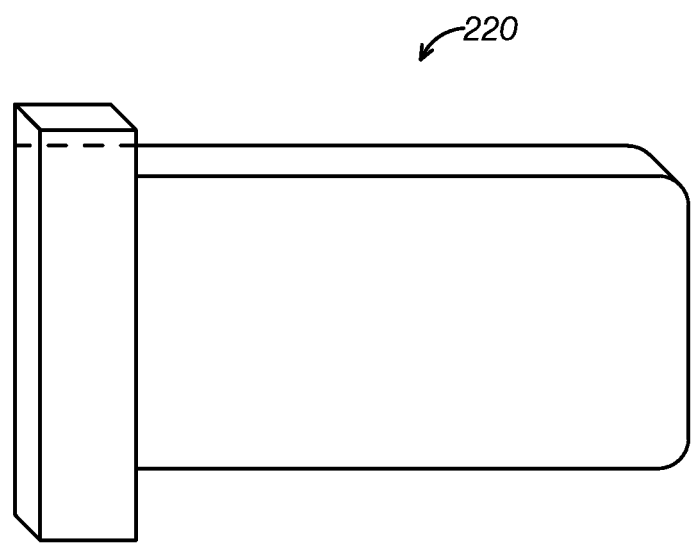
FIG. 20 illustrates a perspective view of an exemplary fluid collector usable in the rapid diagnostic test device of FIG. 16.

The fluid collector 220, as shown in FIG. 20, may be formed of various materials and shapes, as described above, that can collect and contain a liquid sample. Typically, the fluid collector 220 is formed from a porous, deformable material such that, when depressed by the cap 218, the fluid collector 220 may release at least a portion of the fluid (sample) contained therein toward the conjugate color pad 272 of the test strip 270.

Referring now to FIGS. 21 through 24, the use of the test device 210 will be described according to an exemplary embodiment of the present invention.

A sample, such as a body fluid, can be collected on the fluid collector 220. In one embodiment, saliva may be collected from a person onto the fluid collector 220. In some embodiments, the fluid collector 220 may be already held in the inlet 260 of the test device 210 while the sample is obtained. In other embodiments, the sample may be placed onto the fluid collector 220 and then the fluid collector 220 may be placed into the inlet 260 of the test device 210. In still other embodiments, the fluid collector 220 may only press against the inlet 260 of the test device 210 and compression of the fluid collector 220 may drive fluid into the fluid directing channel 224, 238. Compression of the fluid collector 220 may be achieved by various manners. In some embodiments, sliding the cap 218 onto the device 210 may compress the fluid collector 220. In other embodiments, the squeezing portion 300 of the cap 218 may be squeezed to drive fluid out of the fluid collector 220 and into the inlet 260 of the test device 210.

One or more test strips 270 may be disposed in the test device 210. The test strips 270 can include a substrate 276 onto which a porous material 274 is disposed. Each test strip 270 may include a plurality of strip lines 274 that may indicate the presence or absence of a particular substance. In other words, each test strip 270 may test for a plurality of substances. For example, each test strip 270 may be capable of testing for five substances. Therefore, when the test device 210 is designed to hold three test strips 270, as shown, such a test device may be capable of testing for 15 substances.

The conjugate color pad 272 may be disposed below the press pad 222 of the top member 212. In some embodiments, a strip press pad 278 may be formed as part of the test strip 270. As the cap 218 is slid onto the test device 210, the cap 218 may squeeze the top member 212 toward the bottom member 214, causing the press pad 222 of the top member to press downward onto the strip press pad 278 and/or the conjugate color pad 272.

Figure 24:
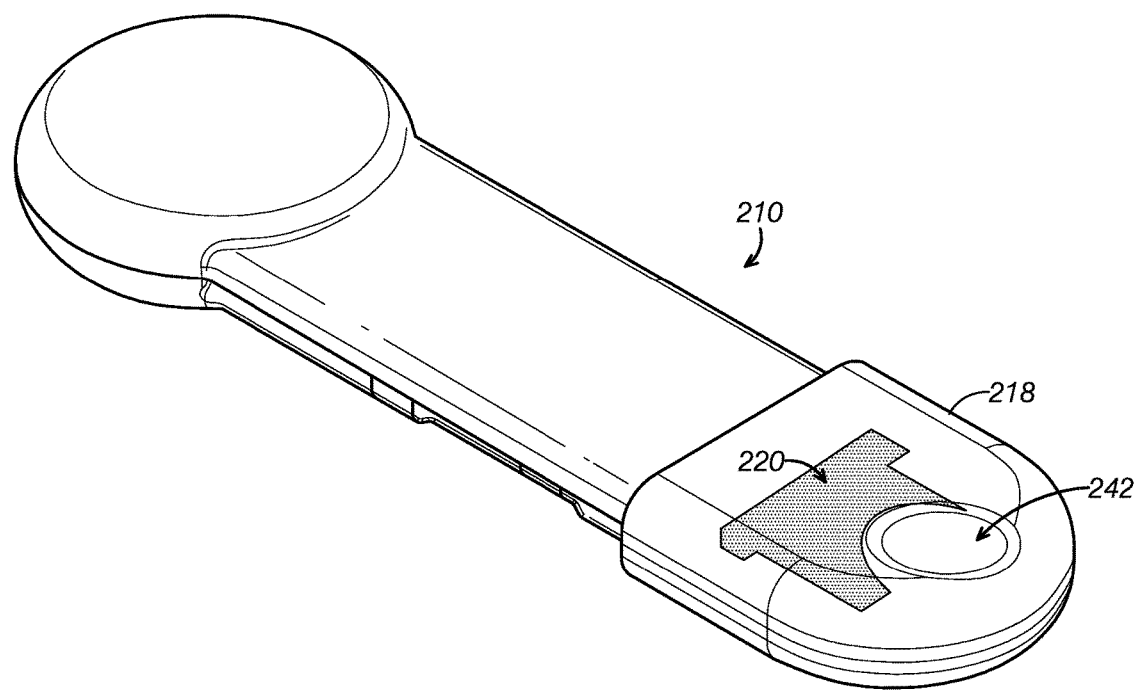
FIG. 24 illustrates a perspective view of the rapid diagnostic test device of FIG. 16 is use with its cap compressing a fluid collector according to an exemplary embodiment of the present invention.

The sample collected in the fluid collector 220 may be forced out of the fluid collector 220 by sliding the cap 218 onto the end of the test device 210, where the notch plates 242, 244 (see also, FIGS. 19A and 19B) compress the fluid collector 220 as shown in FIG. 24. The sample is forced to flow into the fluid directing channel 224, 238 toward the conjugate color pad 272 (see FIGS. 18A, 18B and 22). Excess sample from the fluid collector 220 may be reserved on the bottom of the cap 218 for further testing needs.

The strip press pad 278 may play the role as an auxiliary function to drive chemical mixtures, pre-impregnated on the conjugate color pad 272, out of the conjugate color pad 272 completely. The conjugate color pad 272 provides a source of mobilizable first affinity binding members 280 which may bind with substances in the sample to form a reaction component 282. The strip lines 274 of the test strip 270 can include fixed second affinity binding sites that may react with the reaction component 282 to provide a readable output, indicating the presence or absence of the substance.

The driven flow mechanism of the test device 210 can significantly expedite testing time to about one minute, for example, which is typically about 5 to 20 times faster than conventional rapid test devices.

Because the strip press pad 278 and the press pad 222 of the top member 212 help ensures that the chemical mixtures may be completely driven out of the conjugate color pad 272, the test device 210 of the present invention may be used to provide a quantitative result. For quantitative measurements, in some embodiments, the result window 216 may be formed in both the top member 212 and the bottom member 214, similar to that shown in FIG. 14, thereby allowing a user or a reading device to view the test strip 270 from both sides thereof.

In some embodiments, a mobile communication device, such as a smart phone, may be used, as disclosed in Ozcan et al., U.S. Pat. No. 8,916,390, incorporated herein by reference, to automatically scanned the test strip 270 via the camera of a smart phone. The scanned image can then be interpreted by software to obtain a result and deliver that result to a wireless network, for example.

The test device 210 described above with respect to FIGS. 16 through 24 may incorporate one or more of the features disclosed in the test device 1 described above with respect to FIGS. 1 through 15.

Depending on the analyte being tested and the condition of the fluid specimen, many of the above embodiments have been found to achieve an accuracy of at least 99.99%.

In addition, because a result is obtained so quickly, typically within 1 minute, the test does not require additional buffers or other methods to halt the reaction.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A device for testing a liquid sample for the concentration of at least one analyte, comprising:
   a top member;
   a bottom member connecting to the top member forming an internal cavity therein;
   a fluid directing channel formed in the internal cavity;
   an inlet formed in a first end of the device, the inlet fluidly communicating with the fluid directing channel;
   a press pad formed in the top member adapted to align with a conjugate color pad of a test strip, the press pad configured to deflect downwardly and press against the conjugate color pad of the test strip disposed within the internal cavity; and
   a cap fitting over the first end of the device, the cap configured to press against a fluid collector having the liquid sample disposed therein, thereby driving the fluid sample into the fluid directing channel.

2. The device of claim 1, further comprising side walls disposed from the top member and the bottom member, the side walls defining sides of the fluid directing channel.

3. The device of claim 1, further comprising a plurality of side bars extending along the bottom member, the plurality of side bars forming at least one strip slot configured to retain the test strip therein.

4. The device of claim 3, wherein three strip slots are formed by the plurality of side bars.

5. The device of claim 1, further comprising a result window formed in at least one of the top member and the bottom member.

6. The device of claim 1, wherein the cap includes a squeezing portion and a specimen retention portion.

7. The device of claim 6, wherein an interior of the cap includes at least one ramp directing a first portion of a specimen into the device and a second portion of the specimen into the specimen retention portion.

8. A test system for testing a liquid sample for the concentration of at least one analyte, comprising:
   at least one test strip comprising:
      a conjugate color pad including a source of mobilizable labeled first affinity binding members bindable to the analyte;
      a liquid permeable reaction region including at least one strip line including immobilized second affinity capture binding members bindable to said analyte; and
      a strip press pad aligned with and disposed over the conjugate color pad; and
   a test device comprising:
   a top member;
      a bottom member connecting to the top member forming an internal cavity therein;
      a fluid directing channel formed in the internal cavity containing the test strip;
      an inlet formed in a first end of the device, the inlet fluidly communicating with the fluid directing channel;
      a press pad formed in the top member, the press pad configured to press against the strip press pad and the conjugate color pad of the test strip; and
      a cap fitting over the first end of the device, the cap configured to press against a fluid collector having the liquid sample disposed therein, thereby driving the fluid sample into the fluid directing channel.

9. The system of claim 8, further comprising side walls disposed from the top member and the bottom member, the side walls defining sides of the fluid directing channel.

10. The system of claim 8, further comprising a plurality of side bars extending along the bottom member, the plurality of side bars forming at least one strip slot configured to retain the test strip therein.

11. The system of claim 10, wherein three strip slots are formed by the plurality of side bars.

12. The system of claim 8, further comprising a result window formed in at least one of the top member and the bottom member.

13. The system of claim 8, wherein the cap includes a squeezing portion and a specimen retention portion.

14. The system of claim 13, wherein an interior of the cap includes at least one ramp directing a first portion of a specimen into the device and a second portion of the specimen into the specimen retention portion.

15. The system of claim 8, wherein, when the cap is slid onto the test device, the top member and bottom member deforms to cause the press pad of the top member to exert a further force on the strip press pad and the conjugate color pad.

16. A method for testing for an analyte in a sample, comprising:
- disposing at least one test strip into an internal cavity formed between a top member and a bottom member of a test device;
- sliding a cap onto a first end of the test device to compress a fluid collector to cause the sample to be expelled from the fluid collector into a fluid directing channel formed in the internal cavity;
- directing the fluid from the fluid directing channel to a conjugate color pad of the test strip, the conjugate color pad aligned with and disposed on a press pad of the top member; and
- exerting an additional force on the conjugate color pad of the test strip as the cap is slid further onto the first end of the test device.

17. The method of claim 16, wherein the test strip includes a test strip press pad and wherein the press pad of the top member presses against the test strip press pad as the cap is slid onto the first end of the test device.

18. The method of claim 16, further comprising reading results on the test strip through a result window formed in at least one of the top member and the bottom member.

19. The method of claim 16, further comprising compressing the fluid collector by squeezing a squeezing portion of the cap.

* * * * *